United States Patent [19]

Laborda

[11] Patent Number: 5,644,031

[45] Date of Patent: Jul. 1, 1997

[54] DELTA-LIKE GENE EXPRESSED IN NEUROENDOCRINE TUMORS

[75] Inventor: Jorge Laborda, Silver Spring, Md.

[73] Assignee: The United States of America as represented by the Department of Health and Human Services, Washington, D.C.

[21] Appl. No.: 457,135

[22] Filed: Jun. 1, 1995

Related U.S. Application Data

[62] Division of Ser. No. 989,537, Dec. 11, 1992, abandoned.

[51] Int. Cl.⁶ ............................ C07K 1/00; C07K 14/00; C07K 17/00; G01N 33/48
[52] U.S. Cl. .................... 530/350; 436/63; 436/64
[58] Field of Search ................... 530/350; 436/63, 436/64

[56] References Cited

U.S. PATENT DOCUMENTS 5,491,061  2/1996  Laborda ..................................... 435/6

FOREIGN PATENT DOCUMENTS

WO94/13701  6/1994  WIPO .

OTHER PUBLICATIONS

Knust et al. (1987) EMBO J. 6(3): 761–766.
Laborda et al. (1993) J. Biol. Chem. 268(6):3817–3820.
Smas et al. (1993) Cell 73: 725–734.
Smas et al. (1994) Biochemistry 33: 9257–9265.
Vassin et al. (1987) EMBO J. 6(11): 3431–3440.
Fay, et al., "Two fetal antigens (FA–1 and FA–2) and Endometrial Proteins (PP12 and PP14) Isolated from Amniotic Fluid; Preliminary Observations in Fetal and Maternal Tissues" Eur. J. Obstetrics & Gynecology and Reproductive Biology 29: 73–85 (1988).

Tornehave, et al., "Two fetal antigens (FA–1 and FA–2) and Endometrial Proteins (PP12 and PP14) Isolated from Amniotic Fluid: Localisation in the Fetus and Adult Female Genital Tract" Eur. J. Obstetrics & Gynecology and Reproductive Biology 30: 221–232 (1989).

Jensen, et al., "Studies on the Isolation, Structural Analysis and Tissue Localization of Fetal Antigen 1 and its Relation to a Human Adrenal Specific cDNA, pG2" Human Reproduction 8(4):635–41 (Apr. 1993).

Jensen, et al., "Protein Structure of Fetal Antigen 1 (FA1)" Eur. J. Biochem. 225(1):83–92 (Oct. 1, 1994).

Mark J. Cooper et al, "Human Neuroblastoma Tumor Cell Lines Correspond to the Arrested Differentiation of Chromaffin Adrenal Medullary Neuroblasts," Cell Growth & Differentiation, 1989, pp. 149–159.

Lee J. Helman et al, "Molecular Markers of Neuroendocrine Development and Evidence of Environmental Regulation," Proc. Natl. Acad. Sci. USA, vol. 84, pp. 2336–2339, Apr. 1987.

L. Helman et al., "The Sequence of an Adrenal Specific Human cDNA, pG2", Nucl. Acids Research, vol. 18, No. 3, 1990, p. 685.

Lee et al., Biochimica et Biophysica Acta 1261: 223–232 (1995).

Primary Examiner—Robert A. Wax
Assistant Examiner—Lisa J. Hobbs
Attorney, Agent, or Firm—Foley & Lardner

[57] ABSTRACT

A polynucleotide molecule dlk is expressed in neuroendocrine tumors, including small cell lung carcinoma. A Dlk polypeptide encoded by dlk polynucleotide molecule can be used in detecting the existence of a primary or secondary neuroendocrine tumor. Monoclonal antibodies are produced against Dlk which are useful for detection and therapy of a neuroendocrine tumor.

1 Claim, 4 Drawing Sheets

FIG. 1

```
1A
MOUSE  - |....Signal Peptide....*..|         |---------EGF1---------|         |---------EGF2---------|
           MIATGALLRVLLLLLAFG HS TYG AECDPPCDPQYGFCEADNVCRCHVGWEGPLCDKCVTAPG³CVNGVCKEPW.QCICKDGW
           |||||||||||||||||||| || |||                                                        |||
                                                                                                80
HUMAN  - MTATEALLRVLLLLLAFG IIS TYG AECFPACNPQNGFCEDDNVCRCQPGWQGPLCDQCVTSPG³CLHGLCGEPG³QCICTDGW 1B
                             |---------EGF3---------|                     |---------EGF4---------|
MOUSE  - DGKFCEIDVRACTSTPCANN¹G.TCVDLEKG³QYECSCTPGFS²GKDCQHKAGPCVINGSPCQHGGACVDDEGQASHASCLCPPG
                                                                                            160
HUMAN  - DGELCDRDVRACSSAPCANN¹G³TCVSLDDG³LYECSCAPGYS²¹GKDCQKKDGPCVINGSPCQHGGTCVDDEGRASHASCLCPPG

|---------EGF5---------|                       |---------EGF6---------|
MOUSE  - FSGNFCEIVAATNSCTPNPCENDGVCTD⁴IGGDFRCRCPAGFVDKTCSRPVSNCASGPCQNGGTCLQHTQVSFECLCKPPFMGPT
HUMAN  - FSGNFCEIVA--NSCTPNPCENDGVCTD⁴IGGDFRCRCPAGFIDKTCSRPVTNCASSPCQNGGTCLQHTQVSYECLCKPEFTGLT
                                                                                            240

|....Transmembrane.....|
MOUSE  - CAKKRGASPVQVTHLPSGYGLT²YRLTPGVHELPVQQPEQHILKVS²MKELN¹KSTPLLTEG³QAICFTILG³VLTSLVVLGTVA
HUMAN  - CVKKRALSPQQVTRLPSGYGLA.YRLTPGVHELPVQQPEHR.ILKVS²¹MKELN.KKTPLLTEG³QAICFTILG³VLTSLVVLGTVG
                                                                                            320

MOUSE  - IVFLNKCETWVSNLRYN¹HT²FRKKKNLLLQYNSGEELAVNIIFPEKIDMTTFNKEAGDEEI
                                                                      385
HUMAN  - IVFLNKCETWVSNLRYN.HM.LRKKKNLLLQYNSGEDLAVNIIFPEKIDMTTFSKEAGDEEI
                                                                      383
```

FIG. 2

```
              3         9        15        21        27        33        39        45
              |         |         |         |         |         |         |         |
   1 TCT AAA GGA GGT GGA GAG CGC ACC GCA GCC CGG TGC AGC CCG GTG
  46 CAG CCC TGG CTT TCC CCT CGC TGC GGC CCG TGC CCC CTT TCG CGT
  91 CCG CAA CCA GAA GCC CAG TGC GGC GCC AGG AGC CGG ACC CGC GCC
 136 CGC ACC GCT CCC GGG ACC GCG ACC CCG GCC GCC CAG AGA TGA CCG
 181 CGA CCG AAG CCC TCC TGC GCG TCC TCT TGC TCC TGC TGG CTT TCG
 226 GCC ACA GCA CCT ATG GGG CTG AAT GCT TCC CGG CCT GCA ACC CCC
 271 AAA ATG GAT TCT GCG AGG ATG ACA ATG TTT GCA GGT GCC AGC CTG
 316 GCT GGC AGG GTC CCC TTT GTG ACC AGT GCG TGA CCT CTC CCG GCT
 361 GCC TTC ACG GAC TCT GTG GAG AAC CCG GGC AGT GCA TTT GCA CCG
 406 ACG GCT GGG ACG GGG AGC TCT GTG ATA GAG ATG TTC GGG CCT GCT
 451 CCT CGG CCC CCT GTG CCA ACA ACG GGA CCT GCG TGA GCC TGG ACG
 496 ATG GCC TCT ATG AAT GCT CCT GTG CCC CGG GTT ACT CGG GAA AGG
 541 ACT GCC AGA AAA AGG ACG GGC CCT GTG TGA TCA ACG GCT CCC CCT
 586 GCC AGC ACG GAG GCA CCT GCG TGG ATG ATG AGG GCC GGG CCT CCC
 631 ATG CCT CCT GCC TGT GCC CCC CTG GCT TCT CAG GCA ATT TCT GCG
 676 AGA TCG TGG CCA ACA GCT GCA CCC CCA ACC CAT GCG AGA ACG ACG
 721 GCG TCT GCA CTG ACA TTG GGG GCG ACT TCC GCT GCC GGT GCC CAG
 766 CCG GCT TCA TCG ACA AGA CCT GCA GCC GCC CGG TGA CCA ACT GCG
 811 CCA GCA GCC CGT GCC AGA ACG GGG GCA CCT GCC TGC AGC ACA CCC
 856 AGG TGA GCT ACG AGT GTC TGT GCA AGC CCG AGT CAA CAG GTC TCA
 901 CCT GTG TCA AGA AGC GCG CGC TGA GCC CCC AGC AGG TCA CCC GTC
 946 TGC CCA GCG GCT ATG GGC TGG CCT ACC GCC TGA CCC CTG GGG TGC
 991 ACG AGC TGC CGG TGC AGC AGC CGG AGC ACC GCA TCC TGA AGG TGT
1036 CCA TGA AAG AGC TCA ACA AGA AAA CCC CTC TCC TCA CCG AGG GCC
1081 AGG CCA TCT GCT TCA CCA TCC TGG GCG TGC TCA CCA GCC TGG TGG
1126 TGC TGG GCA CTG TGG GTA TCG TCT TCC TCA ACA AGT GCG AGA CCT
1171 GGG TGT CCA ACC TGC GCT ACA ACC ACA TGC TGC GGA AGA AGA AGA
1216 ACC TGC TGC TTC AGT ACA ACA GCG GGG AGG ACC TGG CCG TCA ACA
1261 TCA TCT TCC CCG AGA AGA TCG ACA TGA CCA CCT TCA GCA AGG AGG
1306 CCG GCG ACG AGG AGA TCT AAG CAG CGT TCC CAC AGC CCC TCT AG
1351 ATT CTT GGA GTT CCG CAG AGC TTA CTA TAC GCG GTC TGT CCT AAT
1396 CTT TGT GGT GTT CGC TAT CTC TTG TGT CAA ATC TGG TGA ACG CTA
1441 CGC TTA CAT ATA TTG TCT TTG TGC TGC TGT GTG ACA AAC GCA ATG
1486 CAA AAA CAA TCC TCT TTC TCT CTC TTA ATG CAT GAT ACA GAA TAA
1531 TAA TAA GAA TTT CAT CTT TAA ATG AG
```

Total number of bases is: 1556.

FIG. 3

```
              3         9        15        21        27        33        39        45
              |         |         |         |         |         |         |         |
   1 GGT GCA ACC CTA GCT TTC TTC CCG CTG GAC GCC CGT GCC CCC TTC
  46 GTG GTC CGC AAC CAG AAG CCC AGC GCA CGC CCC GGA GCA GCC CCT
  91 GCA CCG CCT CCG CTC CCC GGA CCG CGA CCC AGG CCG CCC CGA GAT
 136 GAT CGC GAC CGG AGC CCT CCT GCG CGT CCT CTT GCT CCT GCT GGC
 181 TTT CGG CCA CAG CAC CTA TGG GGC TGA ATG CGA CCC ACC CTG TGA
 226 CCC CCA GTA TGG ATT CTG CGA GGC TGA CAA TGT CTG CAG GTG CCA
 271 TGT TGG CTG GGA GGG TCC CCT CTG TGA CAA GTG TGT AAC TGC CCC
 316 TGG CTG TGT CAA TGG AGT CTG CAA GGA ACC ATG GCA GTG CAT CTG
 361 CAA GGA TGG CTG GGA CGG GAA ATT CTG CGA AAT AGA CGT TCG GGC
 406 TTG CAC CTC AAC CCC CTG CGC CAA CAA TGG AAC TTG CGT GGA CCT
 451 GGA GAA AGG CCA GTA CGA ATG CTC CTG CAC ACC TGG GTT CTC TGG
 496 AAA GGA CTG CCA GCA CAA GGC TGG GCC CTG CGT GAT CAA TGG TTC
 541 TCC CTG CCA GCA CGG AGG CGC CTG CGT GGA TGA TGA GGG CCA GGC
 586 CTC GCA TGC TTC CTG CCT GTG CCC CCC TGG CTT CTC AGG CAA CTT
 631 CTG TGA GAT CGT AGC CGC AAC CAA CAG CTG TAC CCC TAA CCC ATG
 676 CGA GAA CGA TGG CGT CTG CAC CGA CAT CGG GGG TGA CTT CCG TTG
 721 CCG CTG CCC AGC TGG ATT CGT CGA CAA GAC CTG CAG CCG CCC GGT
 766 GAG CAA CTG CGC CAG TGG CCC GTG CCA GAA CGG GGG CAC CTG CCT
 811 CCA GCA CAC CCA GGT GAG CTT CGA GTG TCT GTG CAA GCC CCC GTT
 856 CAT GGG TCC CAC GTG CGC GAA GAA GCG CGG GGC TAG CCC CGT GCA
 901 GGT CAC CCA CCT GCC CAG CGG CTA TGG GCT CAC CTA CCG CCT GAC
 946 CCC CGG GGT GCA CGA GCT GCC TGT TCA GCA GCC CGA GCA ACA CAT
 991 CCT GAA GGT GTC CAT GAA AGA GCT CAA CAA GAG TAC CCC TCT CCT
1036 CAC CGA GGG ACA GGC CAT CTG CTT CAC CAT CCT GGG CGT GCT CAC
1081 CAG CCT GGT GGT GCT GGG CAC CGT GGC CAT CGT CTT TCT CAA CAA
1126 GTG CGA AAC CTG GGT GTC CAA CCT GCG CTA CAA CCA CAC GTT TCG
1171 CAA GAA GAA GAA CCT CCT GTT GCA GTA TAA CAG CGG CGA GGA GCT
1216 GGC GGT CAA TAT CAT CTT CCC CGA GAA GAT TGA CAT GAC CAC CTT
1261 CAA CAA GGA GGC TGG TGA TGA GGA GAT CTA AGC AGC GTT CCC CAC
1306 CCC CAC TCC CAG GCC CTT CAC CCC GAC CCC GAC CCA GGC CCT CTC
1351 TAT TAC CGG GTT CCT TTA GAG CTC TCT ACC GAG TCT GGC TTT TTG
1396 TGG TGG AGT TTG CTC TAT TGT GTG GAA TCG AGT GAA GCC TAT GCT
1441 TAC ATA TAT TGT CTT GTG TTG CTG TGT GCC ATG CTA CCT CGC TAT
1486 CTA AGA ACC CCT TCC TCC CTA TTA ATG CAT GAT AAT GAA TAA TAA
1531 TAA TAA GAA TTT CAT CTC TAA ATG AAA AAA AAA AAA AAA AAA G
```

Total number of bases is: 1573.

FIG. 4

| | | | | | | | | | | |
|---|---|---|---|---|---|---|---|---|---|---|
| Consensus | C | | PC | NGG | C | D | Y | C | C | | G | C |
| dlk | C | | PC | NGG | C | D | Y | C | C | PGF | G | C |
| Delta | C | | PC | NGGTC | | D | Y | C | C | GF | G | C |
| Serrate | C | | PC | NGGTC | | D | F | C | C | G | G | C |
| TAN-1 | C | | PC | NGGTC | | D | Y | C | C | GF | G | C |
| Notch | C | S | PC | NGGTC | | D | Y | C | C | GF | G | C |
| Xotch | C | | PC | NGGTC | | D | Y | C | C | GF | G | C |
| Lin-12 | CL | | C | N G CI | | | Y | C | C | GY | G | C |

EGF mouse    CPSSYDGYCLNGGVCMHIESDLSYT CNCVIGYSGDRC

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 385 amino acids
( B ) TYPE: amino acid
( D ) TOPOLOGY: linear ( v i ) ORIGINAL SOURCE:
( B ) STRAIN: Mouse Dlk ( x i ) SEQUENCE DESCRIPTION: SEQ ID NO:1:

```
Met Ile Ala Thr Gly Ala Leu Leu Arg Val Leu Leu Leu Leu Leu Ala
 1               5                  10                  15

Phe Gly His Ser Thr Tyr Gly Ala Glu Cys Asp Pro Pro Cys Asp Pro
            20                  25                  30

Gln Tyr Gly Phe Cys Glu Ala Asp Asn Val Cys Arg Cys His Val Gly
        35                  40                  45

Trp Glu Gly Pro Leu Cys Asp Lys Cys Val Thr Ala Pro Gly Cys Val
    50                  55                  60

Asn Gly Val Cys Lys Glu Pro Trp Gln Cys Ile Cys Lys Asp Gly Trp
65                  70                  75                  80
```

```
Asp Gly Lys Phe Cys Glu Ile Asp Val Arg Ala Cys Thr Ser Thr Pro
                85              90                  95
Cys Ala Asn Asn Gly Thr Cys Val Asp Leu Glu Lys Gly Gln Tyr Glu
            100             105             110
Cys Ser Cys Thr Pro Gly Phe Ser Gly Lys Asp Cys Gln His Lys Ala
        115             120             125
Gly Pro Cys Val Ile Asn Gly Ser Pro Cys Gln His Gly Gly Ala Cys
    130             135             140
Val Asp Asp Glu Gly Gln Ala Ser His Ala Ser Cys Leu Cys Pro Pro
145             150             155             160
Gly Phe Ser Gly Asn Phe Cys Glu Ile Val Ala Ala Thr Asn Ser Cys
                165             170             175
Thr Pro Asn Pro Cys Glu Asn Asp Gly Val Cys Thr Asp Ile Gly Gly
            180             185             190
Asp Phe Arg Cys Arg Cys Pro Ala Gly Phe Val Asp Lys Thr Cys Ser
        195             200             205
Arg Pro Val Ser Asn Cys Ala Ser Gly Pro Cys Gln Asn Gly Gly Thr
    210             215             220
Cys Leu Gln His Thr Gln Val Ser Phe Glu Cys Leu Cys Lys Pro Pro
225             230                 235             240
Phe Met Gly Pro Thr Cys Ala Lys Lys Arg Gly Ala Ser Pro Val Gln
            245             250             255
Val Thr His Leu Pro Ser Gly Tyr Gly Leu Thr Tyr Arg Leu Thr Pro
            260             265             270
Gly Val His Glu Leu Pro Val Gln Gln Pro Glu Gln His Ile Leu Lys
        275             280             285
Val Ser Met Lys Glu Leu Asn Lys Ser Thr Pro Leu Leu Thr Glu Gly
    290             295             300
Gln Ala Ile Cys Phe Thr Ile Leu Gly Val Leu Thr Ser Leu Val Val
305             310             315             320
Leu Gly Thr Val Ala Ile Val Phe Leu Asn Lys Cys Glu Thr Trp Val
            325             330             335
Ser Asn Leu Arg Tyr Asn His Thr Phe Arg Lys Lys Lys Asn Leu Leu
            340             345             350
Leu Gln Tyr Asn Ser Gly Glu Glu Leu Ala Val Asn Ile Ile Phe Pro
        355             360             365
Glu Lys Ile Asp Met Thr Thr Phe Asn Lys Glu Ala Gly Asp Glu Glu
    370             375             380
Ile
385
```

( 2 ) INFORMATION FOR SEQ ID NO:2:

( i ) SEQUENCE CHARACTERISTICS:
        ( A ) LENGTH: 383 amino acids
        ( B ) TYPE: amino acid
        ( D ) TOPOLOGY: linear ( v i ) ORIGINAL SOURCE:
        ( B ) STRAIN: Human Dlk ( x i ) SEQUENCE DESCRIPTION: SEQ ID NO:2:

```
Met Thr Ala Thr Glu Ala Leu Leu Arg Val Leu Leu Leu Leu Leu Ala
1               5               10                  15
Phe Gly His Ser Thr Tyr Gly Ala Glu Cys Phe Pro Ala Cys Asn Pro
            20              25              30
Gln Asn Gly Phe Cys Glu Asp Asp Asn Val Cys Arg Cys Gln Pro Gly
```

|   |   |   | 35 |   |   |   |   | 40 |   |   |   |   | 45 |   |   |
|---|---|---|---|---|---|---|---|---|---|---|---|---|---|---|---|

Trp Gln Gly Pro Leu Cys Asp Gln Cys Val Thr Ser Pro Gly Cys Leu
     50                      55                      60

His Gly Leu Cys Gly Glu Pro Gly Gln Cys Ile Cys Thr Asp Gly Trp
65                      70                      75                      80

Asp Gly Glu Leu Cys Asp Arg Asp Val Arg Ala Cys Ser Ser Ala Pro
                    85                      90                      95

Cys Ala Asn Asn Gly Thr Cys Val Ser Leu Asp Asp Gly Leu Tyr Glu
                100                     105                     110

Cys Ser Cys Ala Pro Gly Tyr Ser Gly Lys Asp Cys Gln Lys Lys Asp
            115                     120                     125

Gly Pro Cys Val Ile Asn Gly Ser Pro Cys Gln His Gly Gly Thr Cys
        130                     135                     140

Val Asp Asp Glu Gly Arg Ala Ser His Ala Ser Cys Leu Cys Pro Pro
145                     150                     155                     160

Gly Phe Ser Gly Asn Phe Cys Glu Ile Val Ala Asn Ser Cys Thr Pro
                    165                     170                     175

Asn Pro Cys Glu Asn Asp Gly Val Cys Thr Asp Ile Gly Gly Asp Phe
            180                     185                     190

Arg Cys Arg Cys Pro Ala Gly Phe Ile Asp Lys Thr Cys Ser Arg Pro
        195                     200                     205

Val Thr Asn Cys Ala Ser Ser Pro Cys Gln Asn Gly Gly Thr Cys Leu
    210                     215                     220

Gln His Thr Gln Val Ser Tyr Glu Cys Leu Cys Lys Pro Glu Phe Thr
225                     230                     235                     240

Gly Leu Thr Cys Val Lys Lys Arg Ala Leu Ser Pro Gln Gln Val Thr
                    245                     250                     255

Arg Leu Pro Ser Gly Tyr Gly Leu Ala Tyr Arg Leu Thr Pro Gly Val
            260                     265                     270

His Glu Leu Pro Val Gln Gln Pro Glu His Arg Ile Leu Lys Val Ser
        275                     280                     285

Met Lys Glu Leu Asn Lys Lys Thr Pro Leu Leu Thr Glu Gly Gln Ala
    290                     295                     300

Ile Cys Phe Thr Ile Leu Gly Val Leu Thr Ser Leu Val Val Leu Gly
305                     310                     315                     320

Thr Val Gly Ile Val Phe Leu Asn Lys Cys Glu Thr Trp Val Ser Asn
                    325                     330                     335

Leu Arg Tyr Asn His Met Leu Arg Lys Lys Asn Leu Leu Leu Gln
            340                     345                     350

Tyr Asn Ser Gly Glu Asp Leu Ala Val Asn Ile Ile Phe Pro Glu Lys
        355                     360                     365

Ile Asp Met Thr Thr Phe Ser Lys Glu Ala Gly Asp Glu Glu Ile
    370                     375                     380

( 2 ) INFORMATION FOR SEQ ID NO:3:

( i ) SEQUENCE CHARACTERISTICS:
        ( A ) LENGTH: 1556 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: Human Dlk ( x i ) SEQUENCE DESCRIPTION: SEQ ID NO:3:

TCTAAAGGAG GTGGAGAGCG CACCGCAGCC CGGTGCAGCC CGGTGCAGCC CTGGCTTTCC    60

| | | | | | | |
|---|---|---|---|---|---|---|
| CCTCGCTGCG | GCCCGTGCCC | CCTTTCGCGT | CCGCAACCAG | AAGCCCAGTG | CGGCGCCAGG | 120 |
| AGCCGGACCC | GCGCCCGCAC | CGCTCCCGGG | ACCGCGACCC | CGGCCGCCCA | GAGATGACCG | 180 |
| CGACCGAAGC | CCTCCTGCGC | GTCCTCTTGC | TCCTGCTGGC | TTTCGGCCAC | AGCACCTATG | 240 |
| GGGCTGAATG | CTTCCCGGCC | TGCAACCCCC | AAAATGGATT | CTGCGAGGAT | GACAATGTTT | 300 |
| GCAGGTGCCA | TGTCGGCTGG | CAGGGTCCCC | TTTGTGACCA | GTGCGTGACC | TCTCCCGGCT | 360 |
| GCCTTCACGG | ACTCTGTGGA | GAACCCGGGC | AGTGCATTTG | CACCGACGGC | TGGGACGGGG | 420 |
| AGCTCTGTGA | TAGAGATGTT | CGGGCCTGCT | CCTCGGCCCC | CTGTGCCAAC | AACGGGACCT | 480 |
| GCGTGAGCCT | GGACGGTGGC | CTCTATGAAT | GCTCCTGTGC | CCCCGGGTAC | TCGGGAAAGG | 540 |
| ACTGCCAGAA | AAAGGACGGG | CCCTGTGTGA | TCAACGGCTC | CCCCTGCCAG | CACGGAGGCA | 600 |
| CCTGCGTGGA | TGATGAGGGC | CGGGCCTCCC | ATGCCTCCTG | CCTGTGCCCC | CTGGCTTCT | 660 |
| CAGGCAATTT | CTGCGAGATC | GTGGCCAACA | GCTGCACCCC | CAACCCATGC | GAGAACGACG | 720 |
| GCGTCTGCAC | TGACATTGGG | GGCGACTTCC | GCTGCCGGTG | CCCAGCCGGC | TTCATCGACA | 780 |
| AGACCTGCAG | CCGCCCGGTG | ACCAACTGCG | CCAGCAGCCC | GTGCCAGAAC | GGGGGCACCT | 840 |
| GCCTGCAGCA | CACCCAGGTG | AGCTACGAGT | GTCTGTGCAA | GCCCGAGTTC | ACAGGTCTCA | 900 |
| CCTGTGTCAA | GAAGCGCGCG | CTGAGCCCCC | AGCAGGTCAC | CCGTCTGCCC | AGCGGCTATG | 960 |
| GGCTGGCCTA | CCGCCTGACC | CCTGGGGTGC | ACGAGCTGCC | GGTGCAGCAG | CCGGAGCACC | 1020 |
| GCATCCTGAA | GGTGTCCATG | AAAGAGCTCA | ACAAGAAAAC | CCCTCTCCTC | ACCGAGGGCC | 1080 |
| AGGCCATCTG | CTTCACCATC | CTGGGCGTGC | TCACCAGCCT | GGTGGTGCTG | GGCACTGTGG | 1140 |
| GTATCGTCTT | CCTCAACAAG | TGCGAGACCT | GGGTGTCCAA | CCTGCGCTAC | AACCACATGC | 1200 |
| TGCGGAAGAA | GAAGAACCTG | CTGCTTCAGT | ACAACAGCGG | GGAGGACCTG | GCCGTCAACA | 1260 |
| TCATCTTCCC | CGAGAAGATC | GACATGACCA | CCTTCAGCAA | GGAGGCCGGC | GACGAGGAGA | 1320 |
| TCTAAGCAGC | GTTCCCACAG | CCCCCTCTAG | ATTCTTGGAG | TTCCGCAGAG | CTTACTATAC | 1380 |
| GCGGTCTGTC | CTAATCTTTG | TGGTGTTCGC | TATCTCTTGT | GTCAAATCTG | GTGAACGCTA | 1440 |
| CGCTTACATA | TATTGTCTTT | GTGCTGCTGT | GTGACAAACG | CAATGCAAAA | ACAATCCTCT | 1500 |
| TTCTCTCTCT | TAATGCATGA | TACAGAATAA | TAATAAGAAT | TTCATCTTTA | AATGAG | 1556 |

( 2 ) INFORMATION FOR SEQ ID NO:4:

( i ) SEQUENCE CHARACTERISTICS:
        ( A ) LENGTH: 1573 base pairs
        ( B ) TYPE: nucleic acid
        ( C ) STRANDEDNESS: double
        ( D ) TOPOLOGY: linear ( v i ) ORIGINAL SOURCE:
        ( B ) STRAIN: Mouse Dlk ( x i ) SEQUENCE DESCRIPTION: SEQ ID NO:4:

| | | | | | | |
|---|---|---|---|---|---|---|
| GGTGCAACCC | TAGCTTTCTT | CCCGCTGGAC | GCCCGTGCCC | CCTTCGTGGT | CCGCAACCAG | 60 |
| AAGCCCAGCG | CACGCCCCGG | AGCAGCCCCT | GCACCGCCTC | CGCTCCCCGG | ACCGCGACCC | 120 |
| AGGCCGCCCC | GAGATGATCG | CGACCGGAGC | CCTCCTGCGC | GTCCTCTTGC | TCCTGCTGGC | 180 |
| TTTCGGCCAC | AGCACCTATG | GGGCTGAATG | CGACCCACCC | TGTGACCCCC | AGTATGGATT | 240 |
| CTGCGAGGCT | GACAATGTCT | GCAGGTGCCA | TGTTGGCTGG | GAGGGTCCCC | TCTGTGACAA | 300 |
| GTGTGTAACT | GCCCCTGGCT | GTGTCAATGG | AGTCTGCAAG | GAACCATGGC | AGTGCATCTG | 360 |
| CAAGGATGGC | TGGGACGGGA | AATTCTGCGA | AATAGACGTT | CGGGCTTGCA | CCTCAACCCC | 420 |
| CTGCGCCAAC | AATGGAACTT | GCGTGGACCT | GGAGAAAGGC | CAGTACGAAT | GCTCCTGCAC | 480 |

| | | | | | |
|---|---|---|---|---|---|
| ACCTGGGTTC | TCTGGAAAGG | ACTGCCAGCA | CAAGGCTGGG | CCCTGCGTGA | TCAATGGTTC | 540 |
| TCCCTGCCAG | CACGGAGGCG | CCTGCGTGGA | TGATGAGGGC | CAGGCCTCGC | ATGCTTCCTG | 600 |
| CCTGTGCCCC | CCTGGCTTCT | CAGGCAACTT | CTGTGAGATC | GTAGCCGCAA | CCAACAGCTG | 660 |
| TACCCCTAAC | CCATGCGAGA | ACGATGGCGT | CTGCACCGAC | ATCGGGGTG | ACTTCCGTTG | 720 |
| CCGCTGCCCA | GCTGGATTCG | TCGACAAGAC | CTGCAGCCGC | CCGGTGAGCA | ACTGCGCCAG | 780 |
| TGGCCCGTGC | CAGAACGGGG | GCACCTGCCT | CCAGCACACC | CAGGTGAGCT | TCGAGTGTCT | 840 |
| GTGCAAGCCC | CCGTTCATGG | GTCCCACGTG | CGCGAAGAAG | CGCGGGGCTA | GCCCCGTGCA | 900 |
| GGTCACCCAC | CTGCCCAGCG | GCTATGGGCT | CACCTACCGC | CTGACCCCCG | GGGTGCACGA | 960 |
| GCTGCCTGTT | CAGCAGCCCG | AGCAACACAT | CCTGAAGGTG | TCCATGAAAG | AGCTCAACAA | 1020 |
| GAGTACCCCT | CTCCTCACCG | AGGGACAGGC | CATCTGCTTC | ACCATCCTGG | GCGTGCTCAC | 1080 |
| CAGCCTGGTG | GTGCTGGGCA | CCGTGGCCAT | CGTCTTTCTC | AACAAGTGCG | AAACCTGGGT | 1140 |
| GTCCAACCTG | CGCTACAACC | ACACGTTTCG | CAAGAAGAAG | AACCTCCTGT | TGCAGTATAA | 1200 |
| CAGCGGCGAG | GAGCTGGCGG | TCAATATCAT | CTTCCCCGAG | AAGATTGACA | TGACCACCTT | 1260 |
| CAACAAGGAG | GCTGGTGATG | AGGAGATCTA | AGCAGCGTTC | CCCACCCCA | CTCCCAGGCC | 1320 |
| CTTCACCCCG | ACCCCGACCC | AGGCCCTCTC | TATTACCGGG | TTCCTTTAGA | GCTCTCTACC | 1380 |
| GAGTCTGGCT | TTTTGTGGTG | GAGTTTGCTC | TATTGTGTGG | AATCGAGTGA | AGCCTATGCT | 1440 |
| TACATATATT | GTCTTGTGTT | GCTGTGTGCC | ATGCTACCTC | GCTATCTAAG | AACCCCTTCC | 1500 |
| TCCCTATTAA | TGCATGATAA | TGAATAATAA | TAATAAGAAT | TTCATCTCTA | AATGAAAAAA | 1560 |
| AAAAAAAAAA | AAG | | | | | 1573 |

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:5:

Asn  Gly  Gly  Thr  Cys
    1                            5

( 2 ) INFORMATION FOR SEQ ID NO:6:

( i ) SEQUENCE CHARACTERISTICS:
        ( A ) LENGTH: 25 amino acids
        ( B ) TYPE: amino acid
        ( D ) TOPOLOGY: linear ( x i ) SEQUENCE DESCRIPTION: SEQ ID NO:6:

Cys  Pro  Ser  Ser  Tyr  Asp  Gly  Tyr  Cys  Leu  Asn  Gly  Gly  Val  Cys  Met
    1                  5                              10                          15

His  Ile  Glu  Ser  Asp  Leu  Ser  Tyr  Thr
                      20                                    25

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:7:

Cys  Asn  Cys  Val  Ile  Gly  Tyr  Ser  Gly  Asp  Arg  Cys
    1                            5                              10

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

CAAGCCCGAG TTCACAGGTC     20

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:9:

TCGGGGAAGA TGTTGAC     17

DELTA-LIKE GENE EXPRESSED IN NEUROENDOCRINE TUMORS

This application is a divisional of application Ser. No. 07/989,537, filed Dec. 11, 1992, abandoned.

BACKGROUND OF THE INVENTION

The expression of genes during the development of a pluripotent or progenitor cell into a differentiated, mature cell can provide a context for the study of tumorigenic cells whose origin is derived from such progenitor cells. In certain hematopoietic or epithelial tumors, malignant gene expression correlates substantially with the expression observed during normal development of the tissue from which the tumor originates, Gordon et al., *J. Cell Biol.* 108: 1187 (1989); Godal et al., *Adv. Cancer Res.* 36: 211 (1982). In fact, many biological activities of progenitor cells, including cellular migration and tissue remodeling, resemble pathological activities of cancer cells, such as metastases and tumor invasion.

Neuroblastoma, a tumor of the adrenal gland which afflicts persons during early childhood, is another system in which tumor biology correlates with that of normal differentiation and morphogenesis of its progenitor cells (neuroblast). Neuroblastoma is an embryonal tumor that exhibits both undifferentiated and differentiated histopathology. The development of neuroblastoma tumors mimics stages identifiable during histogenesis of its tissue of origin, the adrenal medulla. Cooper et al., *Cell Growth and Diff.* 1: 149 (1989).

During the development of human adrenal medulla neuroblast into mature chromaffin cells, four individual genes are expressed in a sequential pattern. Once a neuroblast is induced to differentiate along a neuroendocrine pathway, the progressive stages of chromaffin maturation are marked by a temporal expression of genes denoted TH, CGA, pG2 and B2M (Cooper, supra. at page 153). Cooper identified that the pattern of gene expression of these four markers in neuroblastoma cells mimics that of normal adrenal neuroblast arrested during three different stages of development.

One of these marker genes, pG2, was identified first in pheochromocytoma, a tumor of the adult adrenal medulla (Helman et al., *PNAS USA* 84: 2336 (1987)). Helman reported that pG2 also is highly expressed normal human adrenal cells.

Helman isolated a full-length cDNA from a human adrenal cDNA library, and identified a corresponding pG2 protein containing 286 amino acids, having a predicted molecular weight of 30,600 daltons (Helman et al., *Nucleic Acids Res.* 18(3): 685 (1990)).

A gene having developmentally-regulated expression, paralleling that of pG2, would be useful for detecting pheochromocytoma or neuroblastoma by genetic methods, especially since pG2 expression is restricted to the adrenal gland in non-malignant tissues.

SUMMARY OF THE INVENTION

It is therefore an object of the present invention to provide a newly-isolated polynucleotide molecule, dlk, which can be employed in genetic assays to provide a method for detection of a primary or secondary pheochromocytoma or neuroblastoma, or identification of a stage of these tumors.

It is also an object of the present invention to provide a method for detecting primary or secondary small cell lung carcinoma (hereafter, SCLC) or for staging tumor progression of SCLC, which employs dlk polynucleotide molecule in genetic assays.

It is a further object to provide a polynucleotide molecule, designated dlk, which encodes a corresponding Dlk polypeptide. Dlk polypeptide is useful for generating monoclonal or polyclonal antibodies having specificity for an epitope of Dlk polypeptide.

Dlk-specific antibodies, and in particular, labeled monoclonal Dlk-specific antibodies, are useful for detection of primary or secondary neuroendocrine tumors. According to the present invention, Dlk-specific monoclonal antibodies conjugated to a toxin are useful for treatment of primary or secondary neuroendocrine tumors, as well.

In accomplishing these and other objects of the invention, there has been provided, in accordance with one aspect of the present invention, an isolated polynucleotide molecule comprising a DNA sequence encoding a Dlk polypeptide.

An object of the present invention is to provide an isolated Dlk polypeptide consisting essentially of the amino acid sequence shown in FIG. 1B (SEQ ID NO:2), or in FIG. 1A (SEQ ID NO:1).

Another object of the present invention is to provide an isolated polynucleotide molecule which encodes a human or mouse Dlk polypeptide consisting essentially of the amino acid sequence shown in FIGS. 1B (SEQ ID NO:2), or FIG. 1A (SEQ ID NO:1), respectively.

A further object of the invention is to provide a method for detecting a tumor which expresses dlk, including the steps of contacting a sample suspected of being tumorigenic with dlk polynucleotide molecule, under conditions permissive of hybridization between dlk polynucleotide molecule and the sample, and detecting hybridization between the polynucleotide molecule and sample.

Yet another object of the invention is to provide a method for detecting a small cell lung carcinoma, including the steps of contacting a sample of bronchial epithelial cells suspected of being tumorigenic with dlk polynucleotide molecule, under conditions permissive of hybridization between dlk polynucleotide molecule and the sample, and detecting hybridization between the polynucleotide molecule and sample.

BRIEF DESCRIPTION OF THE DRAWINGS

FIG. 1 shows an alignment of (A) mouse and (B) human Dlk amino acid sequences (SEQ ID NOS:1 and 2 respectively). Identical amino acids are shown by the character (|). Similar amino acids are indicated by (^) and classified into the following groups: A, S & T; D & E; N & Q; R & K; I, L, M & V; and F, Y & W. Potential biologically significant sites, found in the database PROSITE (accessible commercially through Intelligenetics Inc. (Mountain View, Calif.)), are indicated by numbers: 1. N-glycosylation site; 2. Protein Kinase C phosphorylation site; 3. N-myristylation site; 4. Aspartic acid and asparagine hydroxylation site. Potential sites of cleavage in the signal peptide are indicated by (*).

FIG. 2 shows human dlk DNA sequence (SEQ ID NO:3).

FIG. 3 shows mouse dlk DNA sequence (SEQ ID NO:4).

FIG. 4 shows an alignment of a consensus sequence of dlk EGF-like repeats with EGF-repeats from several invertebrate homeotic genes. As described in Example 3, a dlk EGF-like repeat consensus sequence (SEQ ID NOS:6 and 7) was obtained by alignment of 12 EGF-like repeats of dlk from both human and mouse. This consensus sequence then was aligned with the consensus sequences of several invertebrate homeotic genes (similarly obtained) and mouse EGF. SEQ ID NO:5 is also shown in this figure.

DETAILED DESCRIPTION OF THE PREFERRED EMBODIMENTS

A human polynucleotide molecule, dlk, and a corresponding human polypeptide, Dlk, encoded by dlk, were discovered, isolated and characterized. Human dlk polynucleotide molecule is expressed in pheochromocytoma, neuroblastoma, and SCLC tumors.

Dlk protein is about 383 amino acids in length and has a molecular weight of about 42,000 daltons. In addition to human dlk, other polynucleotide molecules belonging to the dlk family are provided according to the invention, including murine dlk (FIG. 3, SEQ ID NO:4) and a human variant-dlk, isolated from placenta as described herein.

According to the present invention, isolated polynucleotide molecules or fragments thereof belonging to the dlk family are useful to detect SCLC and neuroendocrine cancers. The expression patterns of dlk can be exploited both (1) to detect primary or secondary tumor cells by the presence of dlk and (2) to diagnose the stage of a tumor that expresses dlk, by measuring the level of dlk expression.

Dlk is a transmembrane protein having expression pattern, in normal non-fetal tissues, which is restricted to the adrenal gland. As a consequence, Dlk is a readily accessible target for antibody imaging or therapy of SCLC, pheochromocytoma and neuroblastoma tumors. According to the present invention, antibodies having specificity for Dlk protein are made and employed to detect or treat cells which produce Dlk protein.

Human dlk cDNA comprises a polynucleotide molecule having the sequence shown in FIG. 2 (SEQ ID NO:3), as determined by nucleotide sequence analysis. The open reading frame, nucleotides 174(ATG) - 1322(TAA), is 1149 nucleotides long. Mouse dlk polynucleotide molecule comprises a DNA sequence (SEQ ID NO:4) having an open reading frame, nucleotides 134(ATG) - 1288(TAA), of 1155 nucleotides, as shown in FIG. 3. Murine Dlk protein is about 385 amino acids and has a molecular weight of about 42,000 daltons.

According to the present invention, a variant of human Dlk is identified in which an amino acid is deleted. A cDNA encoding "variant-Dlk," in which amino acid number 347 of the amino acid sequence shown in FIG. 1(B) (SEQ ID NO:2) is deleted, was isolated from a total human placental cDNA library. Missing amino acid number 347 is located in an intracellular domain of the protein. The placental library containing variant-Dlk also contained substantial amounts of the non-variant form, that is, dlk polynucleotide molecule shown in FIG. 1B (SEQ ID NO:2).

dlk polynucleotide molecule was identified by examination of cDNA expression products of human SCLC (hSCLC) lines which were responsive to stimulation with the ligand, gastrin-releasing peptide (GRP), a neuropeptide implicated in the release of gastrin through its interaction with a G-protein-coupled receptor, GRP receptor. GRP (peptide) is a mitogen for normal lung epithelial and SCLC cells, and for murine Swiss 3T3 fibroblasts.

GRP-responsive hSCLC lines were compared with murine fibroblast cell lines that were differentially responsive to GRP. This approach, as detailed in Example 1, yielded a partial length cDNA molecule which hybridized with a 1.6 KbmRNA expressed both in responsive fibroblasts and responsive SCLC lines. A commercial library of Swiss 3T3 fibroblasts was screened with the partial length cDNA, which yielded several clones having 1.6 Kb inserts, which then were sequenced.

A computer search of the databases "Swissprot" and "NBRF Protein," described by Devereux et al., Nuc. Acids Res. 12(1): 387 (1984), indicated a high degree of homology between Dlk and proteins encoded by several homeotic genes, identified in Example 3. Homeotic genes are development-controlling regulatory genes that assign spatial identity to groups of cells with respect to their morphogenic fates. In segmented organisms, for example, homeotic genes are required for the proper morphogenesis of a distinct region (such as a leg, or antennae) and act by controlling the activities of other genes during development. Dlk protein of the present invention exhibited highest homology with the protein Delta, a neurogenic locus involved in normal neural differentiation in Drosophila. Thus, the present protein was designated "Dlk" for being "delta-like."

Mouse and human Dlk protein sequences share 86.2% identity as well as many potential sites of biological importance, including 6 epidermal growth factor (EGF)-like repeats, a transmembrane domain, and a signal peptide domain at the amino terminus. Based upon these structural features, dlk appears to be a new member of the family of EGF-like neurogenic genes of Drosophila, which are involved in developmental decisions of the embryonal ectoderm to differentiate into epidermal or neuronal cells.

The expression pattern of dlk and its sequence homology with homeotic proteins support that dlk functions in the differentiation decisions taken by the cells of the chromaffin lineage. As detailed in Example 2, dlk is expressed in primary and secondary pheochromocytoma and neuroblastoma, and in normal (non-histopathological) human adrenal medulla and placental cells. According to the present invention, SCLC and neuroblastoma are the only tumors known to express dlk as a function of differentiation.

An isolated dlk, dlk-variant, and murine dlk polynucleotide and protein products are employed in diagnostic methods (described further below) and are made according to the following description. Hereafter, the techniques and applications described for dlk polynucleotide molecule (DNA, RNA) and Dlk protein are intended to be useful for DNA, RNA and protein of murine dlk, and of variant-dlk, as well.

A Dlk polypeptide, according to the present invention, is produced by recombinant DNA techniques, such as those set forth generally by Maniatis et al., MOLECULAR CLONING—A LABORATORY MANUAL, Cold Spring Harbor Laboratory (1982). Methods specifically suitable to cloning and the dlk polynucleotide molecule are described in Example 1.

The dlk polynucleotide molecule of FIG. 1 (SEQ ID NO:1) can be cloned into suitable expression vectors and expressed in prokaryotic, insect or eukaryotic expression systems, including Baculovirus or E. coli. For instance, the protein EGF, having similar functional domains as Dlk, was expressed in E. Coli (Boehringer Manheim). With conventional techniques, therefore, a sequence encoding a Dlk protein, can obtained as a cDNA from mRNA from a commercial adrenal medulla or Swiss 3T3 fibroblast library, or from SCLC, neuroblastoma or pheochromocytoma cell lines. The mRNA can be converted to double-stranded DNA using cDNA cloning techniques well-known to the art, including PCR-based techniques. Linkers or tails may be placed on the ends of the double-stranded DNA to provide convenient restriction sites. After restriction digestion, the DNA may be introduced to any site in a vector, such as a plasmid vector, which has been restricted with a restriction enzyme that generates compatible ends. A suitable plasmid vector in this context is pGEX-λ (Pharmacia). Following ligation, by means of standard techniques, the DNA is introduced into a cell, where its expression produces the desired protein.

Alternatively, a Dlk polypeptide is produced using a commercially available in vitro translation kit from NEN (Boston, Mass.), as detailed in Example 1. This kit employs a translation system (including ribosomes, polymerases, amino acids, etc.) derived from rabbit reticulocyte lysates to express dlk mRNA.

The term "isolated" is used in connection with dlk polynucleotide molecule to indicate that such a molecule is free of proteins with which it is normally associated, such as histones. An isolated form of the dlk is substantially free of other DNA that does not function to regulate, promote, enhance or otherwise modulate its expression.

The term "isolated," with reference to Dlk protein, connotes a polypeptide that is free of other proteins with which it is normally associated.

An isolated dlk polynucleotide molecule is useful in detection of primary SCLC and in identifying metastatic spread of SCLC and other neuroendocrine cancers. More specifically, a method of tumor detection is provided by the present invention which includes the steps of contacting a sample suspected of containing a tumor with a dlk polynucleotide molecule, and detecting expression of dlk polynucleotide products (DNA, RNA, mRNA) in non-adrenal cells. Detection of a dlk polynucleotide product diagnoses the cells as metastatic cells (secondary tumor) of neuroblastoma, pheochromocytoma or SCLC, or as a primary tumor of SCLC.

In addition to tumor detection, accomplished by detection of dlk-expressing cells, the identity of a detected tumor is determined. After recognition of dlk-expression, a tumor type is determined by detecting a tumor-specific marker, tumor-specific morphology, or by presentation by the patient of a clinical pathology that is distinctly associated with any of the tumors selected from the group including neuroblastoma, pheochromocytoma or SCLC. For example, information such as the identification of a cellular marker, histological feature or disease symptom which is specific to one of the tumors of neuroblastoma, pheochromocytoma or SCLC, is recognized.

If dlk expression is detected in cells of a sample taken from bronchial epithelial tissue or tissue removed from the lung, the detection identifies the existence of a primary SCLC. It is preferred that a second step of confirming the origin of the detected dlk-expressing tumor cells as SCLC be performed by detection of a marker, histological feature, or presentation of a distinctive symptom associated with this tumor. For example the histology of an "oat cell" commonly identified with SCLC is detected to confirm the presence of SCLC.

dlk expression is detected by hybridization with dlk polynucleotide molecule. This method includes the steps of contacting a sample suspected of being tumorigenic with dlk polynucleotide molecule and detecting the presence of hybridization between the polynucleotide molecule and sample. A positive hybridization indicates that the sample is tumorigenic.

The polynucleotide molecule or "dlk probe" used to hybridize to dlk expressed in the sample is a labeled fragment of dlk, or preferably a full-length dlk DNA molecule which will hybridize to mRNA or DNA from normal adrenal and neuroendocrine tumor cells. Probes complementary to dlk are prepared by conventional methods, and are preferably allowed to hybridize to mRNA or DNA, using conventional in situ techniques, to a sample (embedded on a microscope slide by means of a standard fixative). Unhybridized probe is removed by nuclease.

In situ techniques which are known in the art may employ the use of fluorescent and radiolabels which can be easily quantitated by fluorescence microscopy or autoradiography, respectively. Generally, fluorescent labels will be preferred. Another labeling technique may employ enzymatic tags which generate readily quantifiable colorimetric or chemiluminescent signals. The intensity of hybridization detected reflects the amount of dlk within the cells of the tissue.

RNA ("Northern") blotting is employed using a dlk polynucleotide molecule of the invention. According to this method, RNA is isolated from tissue by any of a number of standard procedures (Lehrach, H., *Biochemistry*, 16: 4743 (1975)). RNA is subjected to denaturing gel electrophoresis and transferred to nitrocellulose or other support matrix. The dlk mRNA can be detected by hybridization of radioactively or non-radioactively labelled dlk, or dlk fragments, preferably under high stringency conditions, such as recognized by a scientist in this field. The amount of hybridization can be quantified by densitometric methods.

In yet another embodiment of the present invention, the polymerase chain reaction ("PCR") is used to detect dlk DNA or mRNA in a sample. To perform PCR, a pair of dlk sequence specific primers is employed, which hybridize to opposite strands of the dlk gene at offset positions on the double helix. Such primers, taken from the dlk polynucleotide sequences provided in accordance with the invention, represent fragments which preferably are unique to dlk, e.g. sequences having low homology with other proteins than Dlk. Two exemplary dlk-specific primer sequences useful in this context include the following sequences (SEQ ID NOS:8 and 9 respectively), which encode a portion of the intracellular region of Dlk:

5'-CAA GCC CGA GTT CAC AGG TC-3'
5'-TCG GGG AAG ATG TTG AC-3'.

Other such primer pairs can be selected and utilized, as well.

The primers provide initiation points for DNA synthesis. In the presence of DNA polymerase, the four nucleotide triphosphates ("NTPs") and other necessary co-factors, all of which are well known to the art, new DNA strands are synthesized complementary to the templates which hybridized with the primers. Several rounds of synthesis are carried out, with allowance for denaturation of the double stranded products between rounds. Preferably, a thermal stable DNA polymerase is used so that it is not necessary to add enzyme anew for each round of synthesis.

The PCR produces a double stranded DNA amplification product which has the same sequence as the original stretch of the dlk DNA defined by the ends of the primer pair sequences. The amount of PCR product indicates the amount of dlk DNA or dlk mRNA in the sample. The product can be detected by a variety of methods well-known in the art. Where such products are produced in a test tube, or the like, they can be resolved by agarose or polyacrylamide electrophoresis and detected by fluorescence staining, such as ethidium bromide. Alternatively, one of the NTPs may be labelled and the PCR products may be determined by measuring incorporation of the labeled NTP. A variety of other methods for resolving, detecting and measuring the amount of PCR product are well-known to the art that are suitable for use in the present invention.

PCR may be rendered specific for dlk DNA or dlk mRNA in situ and in liquid PCRs. For instance, RNAse or DNAse may be used to remove one template or the other from the sample, and the use of primers that distinguish between the gene and the message, for example, a primer that hybridizes to a sequence in the untranscribed region of the promoter will be gene specific.

Other techniques suitable to the claimed methods are readily apparent to the skilled artisan and can include Nuclease Protection Assays, ELISA and Western blotting. Several assay techniques which are based upon immunological reactions between antigens and antibodies are contemplated by the invention. In particular, assays which use antibodies having specificity for Dlk protein are useful to detect cells which produce Dlk protein.

Antibodies having specificity for Dlk-expressing cells are obtained by stimulating the immune system of an animal with Dlk protein. In this context, the term "antibody" encompasses monoclonal and polyclonal antibodies. Such an antibody can belong to any antibody class (IgG, IgM, IgA, etc.). According to the present invention, an entire Dlk polypeptide is injected into an animal for the purpose of obtaining polyclonal antibodies, or for obtaining lymphocytes or spleen cells for production of monoclonal antibodies.

The general techniques of monoclonal antibody (Mab) production, such as described by Kohler and Milstein, Nature 256:495 (1975), are applied to produce a monoclonal antibody having specificity for Dlk protein. This procedure includes the steps of isolating lymphocytes of an animal which has been sensitized or injected with Dlk polypeptide, fusing them with myeloma cells to produce hybridomas, then screening the hybridomas for production of "anti-Dlk antibodies" which bind preferentially to or exhibit binding specificity for Dlk polypeptide.

"Antibody" also encompasses fragments, like Fab and F(ab')$_2$, of anti-Dlk antibodies, and conjugates of such fragments, and so-called "antigen binding proteins" (single-chain antibodies) which are based on anti-Dlk antibodies, in accordance, for example, with U.S. Pat. No. 4,704,692, the contents of which are hereby incorporated by reference. Alternatively, Mabs or a fragment thereof within the present invention can be produced using conventional procedures via the expression of isolated DNA which codes for variable regions of such an Mab in host cells like E. coli, see, e.g., Ward et al., Nature 341: 544–546 (1989), or transfected murine myeloma cells. See Verhoyen et al., BioAssays 8: 74 (1988); Gillies et al., Biotechnol. 7: 799–804 (1989); Nakatani et al., Biotechnol. 7:805–10 (1989).

Assays in which the above antibodies are employed can include enzyme-linked immunosorbent assay (ELISA), radioimmunoassays, immunoelectrophoresis, and the like. Also useful diagnostically are immunohistochemical techniques which employ monoclonal antibodies of known, specific reactivities.

In accordance with this aspect of the present invention, a sample is obtained from a person to detect: (1) a small cell lung carcinoma, by removing a body fluid or tissue suspected of harboring a tumor, such as alveolar, bronchiolar, or respiratory epithelial cells obtained from a bronchial wash, nasopharyngeal aspirates, throat swabs or the like; (2) a metastasized neuroendocrine tumor, by biopsy, taken from tissue other than the adrenal gland (including cortex and medulla). Immuno-histochemical studies can be performed on such cells using a monoclonal antibody specific for Dlk.

Diagnostic applications of these antibodies are exemplified, according to the present invention, by the use of a kit containing an anti-Dlk antibody, which undergoes a reaction with a biological sample to detect Dlk protein expression. Such a reaction involves the binding of anti-Dlk antibody to Dlk antigen, under conditions permissive of binding. The observation of an antibody-antigen complex in a biological sample indicates a positive result. A kit of this sort could be used to detect the extent of expression of Dlk in a particular biological sample from an individual, animal, or cell line.

Such an immunodiagnostic kit can include anti-Dlk antibody and a receptacle for containing the antibody in a sterilized form. The kit can further include anti-isotype serum antibody which recognizes the anti-Dlk antibody (Fc portion) and which is conjugated to a label, such as an enzyme or fluorescent moiety.

In a preferred embodiment, a radiolabeled anti-Dlk antibody is provided. Such an antibody, preferably a monclonal antibody, is administered to an animal or person for imaging purposes. After a suitable period of time for the administered antibodies to bind Dlk expressing cells, a gamma camera machine is applied to detect the presence of labeled antibodies within the organism. Such a procedure provides information as to where in the organism a primary or secondary Dlk-expressing neuroendocrine tumor is located.

A therapeutic application of anti-Dlk monoclonal antibodies includes administration of anti-Dlk immunotoxins. Conjugation of an anti-Dlk monoclonal antibody to a toxin, such as Psuedomonas exotoxin or other toxins commonly conjugated to an antibody by means of a conventional antibody-toxin linkage. Hertler et al., J. Clin. Oncol. 7(12): 1932 (1989), describe methodologies for creating an antibody-toxin linkage, and is incorporated by reference herein. Thus, the anti-Dlk monoclonal antibody-toxin conjugates described are administered to an individual to target and selectively kill dlk-expressing cells present in neuroendocrine tumors.

Similarly, a kit is provided which contains anti-Dlk immunotoxins in a receptacle. A kit can include the anti-Dlk immunotoxins and a pharmaceutical excipient in a receptacle.

The present invention is further described with reference to the following, illustrative examples. Unless defined otherwise, all technical and scientific terms used herein have the same meaning as commonly understood by one of ordinary skill in the art of the invention. Although any methods and materials similar or equivalent to those described herein can be used in the practice of the invention, the preferred methods and materials have been described. Unless mentioned otherwise, the techniques employed or contemplated herein are standard methodologies known to the art. The materials, methods and examples are illustrative only and not limiting.

Example 1

IDENTIFICATION OF dlk POLYNUCLEOTIDE AND POLYPEPTIDE MOLECULES

Identification of dlk

In investigating molecules associated with the gastrin-releasing peptide (GRP) responsive phenotype, s were identified which both were (1) expressed differentially between responsive murine Swiss and unresponsive murine Balb/c 3T3 fibroblasts, and (2) expressed in GRP-responsive human SCLC cell lines. The rationale for this approach was that gene products correlated with a GRP-responsive phenotype would be missing from Balb/c and unresponsive SCLC cell lines, but present in Swiss 3T3 fibroblasts and responsive SCLC cell lines.

A differential library was constructed that enriched for clones expressed in Swiss 3T3 but not in Balb/c 3T3 fibroblasts. The differential library of Swiss 3T3 compared with Balb/c 3T3 fibroblasts was constructed as explained in detail in Timblin et al., Nucleic Acids Res. 18: 1587 (1990). RNA isolation, electrophoresis, northern blots, and hybridization techniques were performed as described in Davis, et al., BASIC METHODS IN MOLECULAR BIOLOGY, Elsevier, N.Y., (1986). The probes were labeled with $^{32}$P dCTP (Amersham, Arlington Heights, Ill.) by the method of random primer as described in Ausubel et al., CURRENT PROTOCOLS IN MOLECULAR BIOLOGY, John Wiley and Sons, N.Y. 3.5.9–3.5.10 (1991).

A partial length clone (150 nucleotides long) isolated from this differential library hybridized with a 1.6 kilobase mRNA which showed an expression pattern which matched with the two screening requirements. This partial length clone was used to screen a commercial oligo dT-primed library of Swiss 3T3 fibroblasts in λZAPII vector (Stratagene (La Jolla, Calif.)), to obtain a full length clone.

Screening procedures and plasmid rescue of positive λZAPII clones were performed following the manufacturer's Stratagene) protocol, as described by Short et al., Nuc. Acids Res. 16:7583 (1988). Several clones with inserts around 1.6 kilobasepairs were obtained.

DNA Sequencing

Rescued plasmids were sequenced with Sequenase (USB, Cleveland, Ohio) by the chain termination method, according to the manufacturer's protocol described by Tabor et al., J. Biol. Chem. 214: 6447 (1989). Nucleotide sequence analysis of the s defined an open reading frame of 1155 nucleotides, encoding a putative protein (Dlk) of 385 amino acids with a molecular weight of 41,320 daltons. This open reading frame was classified as coding by both Fickett's and Shepherd's methods. Fickett et al., Nucleic Acids Res. 10: 5303 (1982); Shepherd et al., Meth. Enzymol. 188:180 (1990). The open reading frames were identified by software programs implementing these methods (PC/Gene software package, Intelligenetics Inc. (Mountain View, Calif.); A. Bairoch, Ph.D thesis, University of Geneva, (1990)).

In vitro Translation of Dlk Polypeptide

In vitro translation assays from mouse dlk mRNA were performed using a rabbit reticulocyte lysate system from NEN (Boston, Mass.), according to manufacturer's protocol, as described by Lockhard et al., Biochem. Biophys. Res. Comm. 37:204 (1969).

dlkmRNA was selected by hybridization of poly A$^+$ RNA from Swiss 3T3 fibroblasts with denatured full-length dlk immobilized on nitrocellulose filters. (dlk mRNA was selected by hybridization of 2 μg of poly A$^+$ Swiss 3T3 RNA with 5 μg of nitrocellulose-immobilized denatured dlk The RNA bound was eluted by boiling. Mouse dlk mRNA was also prepared in vitro using two different full length dlk s cloned in pGEM4Z (Promega). These three mRNAs were used as templates for in vitro translation.

Labeled proteins were analyzed in a 12% polyacrylamide gel followed by fluorography. A protein band of around 42 kilodaltons was present in all three samples, in agreement with the molecular weight of Dlk polypeptide, predicted from its sequence.

A Comparison between mice and humans

Mouse and human dlk polynucleotide sequences are 86.2% identical and 90.1% similarity in their amino acid sequence. They share many potential sites of biological activity, including 6 EGF-like repeats (highly homologous to those found in invertebrate neurogenic proteins) an integral transmembrane domain and a signal peptide domain.

The structural characteristics of dlk were analyzed with the program PC/Gene (Intelligenetics Inc. (Mountain View, Calif.), A. Bairoch, Ph.D thesis, University of Geneva (1990)). The transmembrane domain was found with the program RAOARGOS, implementing the method of Rao and Argos, Biochim. Biophys. Acta 869: 197 (1986). The signal peptide was analyzed with the program PSIGNAL, according to the method of Von Heijne, Nucleic Acids Res. 14: 4683 (1986).

Example 2

A COMPARISON BETWEEN pPG2 and dlk GENE EXPRESSION IN MICE, & dlk GENE EXPRESSION IN HUMANS In normal tissues of human, mouse and hamster origin, dlk expression was detected according to the present invention, only in adrenal and placental tissue. Similarly, pG2 expression was known to be restricted to adrenal gland in normal human tissues.

dlk mRNA was detected by Northern analysis in human and rat pheochromocytoma (PC12) cell lines. pG2 was identified in pheochromocytoma cell lines by Helman et al., PNAS USA 84:2336 (1987).

According to the present invention, dlk was detected in neuroblastoma (SK-N-SH) cells. pG2 expression in neuroblastoma cell lines was detected in differentiated cells, but absent from undifferentiated neuroblastoma cell lines. Cooper et al., Cell Growth and Diff. 1:149 (1989).

In addition, other cells which express dlk identified by the present invention include certain SCLC cell lines. Also, murine Swiss 3T3 fibroblasts were found to express dlk, by using human dlk to probe under high stringency conditions. Balb 3T3 fibroblasts RNA were negative for dlk expression under these conditions.

To explore the relationship between mouse dlk and human pG2, s were isolated and characterized from a λgt10 human adrenal gland library (Clontech, Palo Alto, Calif.) and screened according to the manufacturer's protocol, using mouse dlk as a hybridization probe. Even under low stringency conditions, no s were isolated which coded for proteins with structural characteristics similar to those reported for pG2. Positive λ clones were subcloned into PGEM4Z (Promega, Madison Wis.) and sequenced according to the method of Example 1. Sequence data from several full-length clones which were isolated indicated that these s showed a 82.1% sequence identity with mouse dlk and coded for the human counterpart of the mouse dlk protein (FIG., SEQ ID NOS:1 and 2).

Dlk's structural characterization is very different than that predicted for pG2 protein (Helman et al., supra. (1987)), which consists of a 286 amino acid sequence (about 30 kDa), contains no EGF-like repeats and no signal peptide or transmembrane domains. This was so, despite a finding of an 81.2% nucleotide sequence identity of dlk with pG2 (adrenal gland cDNA library, Helman et al., supra (1990)), as determined using nucleotide sequence homology analysis (GENBANK and EMBL databases). It is assumed that pG2 is identified correctly as the dlk polynucleotide molecule shown in FIG. 1.

Example 3 dlk/Dlk HOMOLOGY WITH OTHER GENES & PROTEINS dlk shows a high degree of homology with the EGF-like neurogenic genes of Drosophila, which are involved in the decisions taken by the cells of the embryohal ectoderm to differentiate into epidermal or neuronal cells. Genes which were found to have highest homology to Dlk include: Delta, Notch and Serrate of *D. melanogaster*, lin-12 and glp1 of *C. elegans*, and uEGF1 of the sea urchin. Although the degree of homology varied between the individual proteins and Dlk, regions of maximum homology exhibited up to 33% amino acid identity, which rose to around 75%, with allowance for conservative amino acid substitutions.

FIG. 4 shows the alignment of mouse or human dlk EGF-like repetitive sequences (SEQ ID NOS:6 and 7) with consensus sequences of EGF sequence repeats (including SEQ ID NO:5) of several proteins. The alignment of the EGF-like repeats was done using the program CLUSTAL, described by Higgins et al., *Gene* 73: 237 (1988). The sites of potential biological importance were analyzed with the program PROSITE. Residues well conserved among homeotic genes also are conserved in dlk, confirming dlk as a member of the family of EGF-like homeotic genes. The amino acid sequence and structure of the EGF-like repeats, as well as the overall structure of dlk, are more related to the invertebrate homeotic genes than to other vertebrate non-homeotic EGF-like proteins, such as EGF-precursor, TGFα, the α, β1 and β2 chains of laminin, coagulation factors, or complement proteins, previously thought to be the mammalian counterparts of the invertebrate homeotic genes.

dlk gene was found present in species ranging from birds to human, including: yeast, Drosophila, Xenopus, mouse, rat, rabbit, chicken, dog, cow, monkey and human. However, despite the structural homology with invertebrate proteins, dlk gene is absent from invertebrates and low vertebrates.

The program PCOMPARE, described by Needleman et al., *Mol. Biol.* 48:443 (1970), included in PC/Gene was used for analysis of homology. In this method, the optimal alignment score between two proteins were compared with the statistical distribution of 100 random alignments. An alignment score of greater than 5 positive standard deviations from the mean random alignment distribution was considered significant, particularly when no functional or structural relationship between the proteins compared is known. Representative alignment scores were determined: Delta, 20.2; Serrate, 19.7; TAN-1, 16.2; Notch, 14.6; Xotch, 13.6; Drosophila Laminin β2, 6.3; mouse Laminin β2, 4.1; human coagulation factor XII, 2.8; and human EGF precursor, 0.6.

Example 4 dlk EXPRESSION: NORTHERN BLOT mRNA ANALYSIS

Expression of dlk was detected by Northern analysis in SCLC lines NCI-H510, NCI-H69 and NCI-N592; in human neuroblastoma line SK-N-SH, and in the rat pheochromocytoma PC-12 cell line. Twenty μg of total RNA or 2 μg of poly A$^+$ were run in a 1% agarose gel and then blotted on a nitrocellulose filter (described in Ex. 1).

A 1.6 Kb band corresponding to dlk was observed only in the SCLC cell lines NCI-N592, NCI-H69 and NCI-H510, and in Swiss 3T3 fibroblasts. Mouse Swiss 3T3 fibroblast RNA also showed a high degree of expression of dlk, even if the hybridization was performed at high stringency with human dlk as a probe. Similar results were obtained using mouse dlk as a probe. Balb/c 3T3 fibroblast RNA was negative for dlk expression under these conditions. Ewing's sarcoma cell lines SK-ES-1, A4573 and TC106 did not express dlk.

In normal tissues of mouse, hamster, and human origin dlk expression was detected exclusively in the adrenal gland.

---

What is claimed is:

1. An isolated Dlk polypeptide consisting essentially of the amino acid sequence shown in FIG. 1B (SEQ ID NO:2).

* * * * *